(12) United States Patent
Lizardi et al.

(10) Patent No.: US 8,870,891 B2
(45) Date of Patent: Oct. 28, 2014

(54) ACL RECONSTRUCTION TUNNEL GAUGE AND METHOD

(75) Inventors: Jose Lizardi, Raynham, MA (US); David Spenciner, Raynham, MA (US)

(73) Assignee: DePuy Mitek, LLC, Raynham, MA (US)

( * ) Notice: Subject to any disclaimer, the term of this patent is extended or adjusted under 35 U.S.C. 154(b) by 360 days.

(21) Appl. No.: 13/168,104

(22) Filed: Jun. 24, 2011

(65) Prior Publication Data

US 2012/0330323 A1    Dec. 27, 2012

(51) Int. Cl.
*A61B 17/58* (2006.01)
*A61B 17/60* (2006.01)
*A61F 2/00* (2006.01)
*A61B 19/00* (2006.01)
*A61B 5/107* (2006.01)
*A61B 17/16* (2006.01)
*A61F 2/08* (2006.01)

(52) U.S. Cl.
CPC ............ *A61B 19/46* (2013.01); *A61B 17/1675* (2013.01); *A61B 2019/462* (2013.01); *A61F 2002/0882* (2013.01); *A61F 2/0805* (2013.01); *A61F 2002/0852* (2013.01); *A61B 5/1076* (2013.01)
USPC ........................................ 606/102

(58) Field of Classification Search
USPC ............................................ 606/102, 96–98
See application file for complete search history.

(56) References Cited

U.S. PATENT DOCUMENTS

| 5,306,301 | A | 4/1994 | Graf |
| 7,134,216 | B2 * | 11/2006 | Rupp et al. ............... 33/512 |
| 2005/0071004 | A1 | 3/2005 | Re et al. |
| 2008/0188935 | A1 | 8/2008 | Saylor |
| 2009/0228015 | A1 | 9/2009 | Ellis |
| 2012/0203237 | A1 * | 8/2012 | Bryan et al. ............ 606/102 |

FOREIGN PATENT DOCUMENTS

| DE | 10312755 A1 | 10/2003 |
| EP | 1206924 A1 | 5/2002 |
| WO | WO 2009111539 A1 | 9/2009 |

OTHER PUBLICATIONS

Smith & Nephew, "Anatomic ACL Reconstruction using the Endobutton Indicator Selection Device", vol. 1, Issue 3, Mar. 2010, pp. 1-5.
Smith & Nephew Endoscopy—EndoButton* CL, Retrieved from the internet: <URL: http://endo.smith-nephew.com/au/Standard.asp?NodeID=2715.
Rosenberg, Thomas D., Smith & Nephew EndoButton* CL Fixation System, "ACL reconstruction with the ACUFEX* Director Drill Guide and EndoButton* CL Fixation System", 1999, 2005 Smith & Nephew, Inc., pp. 1-12.

* cited by examiner

*Primary Examiner* — Kevin T Truong
*Assistant Examiner* — Olivia C Chang (57) ABSTRACT

A depth gauge and method provide for accurate measurement of a socket portion of a bone tunnel in an ACL reconstruction.

7 Claims, 13 Drawing Sheets

ACL RECONSTRUCTION TUNNEL GAUGE AND METHOD

BACKGROUND OF THE INVENTION

1. Field of the Invention

The invention relates to a system and method for reconstructing an anterior cruciate ligament (ACL) and more particularly to a method and gauge for dimensioning a femur tunnel in such a reconstruction.

2. Description of the Related Art

An injured ACL is commonly reconstructed by placing a replacement graft through tunnels prepared in a patient's tibia and femur. In one type of such procedure described in U.S. Pat. No. 5,306,301, the contents of which are incorporated herein by reference, a tunnel is prepared in the femur from a position at or near the patellar surface up through a portion of the femur and exiting through the side of the femur at a superior location. A graft is looped over a loop attached to an elongated bar. The bar is able to pass in one direction up through the tunnel and then out adjacent the superior end of the tunnel. The bar is reoriented such that it will not pass back through the tunnel and is positioned against the femur with the loop and graft hanging down into the tunnel therefrom. The tunnel has sufficient diameter at its inferior portion to accommodate the graft. The tunnel is preferably made narrower at the superior portion, which carries only the loop and not the graft, to minimize bone removal. For convenience, the inferior portion of the tunnel can be termed the socket. Determining a proper depth of the socket quickly, accurately and easily is desired.

SUMMARY OF THE INVENTION

An instrument according to the present invention provides for determining a depth of a bone tunnel in an ACL reconstruction. The instrument comprises a measuring pin having an elongated body having a first end and a first indicia spaced apart from the first end. A first tube co-axially receives the first end of the measuring pin body, the first tube having in internal diameter sized to accommodate the measuring pin body first end, an open first end and a second end. A second tube at the first tube second end has an internal diameter larger than the first tube internal diameter and an first end connected to the first tube second end. A measuring block is disposed at least partially within the second tube and has an abutment and a socket depth scale indicia thereon. A first indicator on the second tube is oriented relative to the socket depth scale indicia being oriented such that when the measuring pin body first end abuts the measuring block abutment the alignment of the indicator and the socket depth scale indicia provides a reading indicative of a desirable depth of the bone tunnel.

Preferably, the measuring block is biased toward the first tube. Also preferably, the first indicator is the second tube second end. Preferably, a loop size indicia is provided thereon.

Preferably, the reading on the socket depth scale indicia represents the distance between the first indicia and the first tube first end minus a loop size indicated by the loop size indicia plus a predetermined flip length. The flip length is a distance beyond the femur necessary to reorient an elongated bar carrying a loop from which the graft is suspended into the bone tunnel from an orientation which allows it to pass through the bone tunnel into a sideways orientation which prevents its passage back into the bone tunnel.

Preferably, a second loop size indicia indicating a different value than the loop size indicia and a second socket depth indicia associated therewith. Accordingly, the reading on the socket depth scale indicia represents the distance between the first indicia and the first tube first end minus a loop size indicated by the loop size indicia plus a predetermined flip length and the reading on the second socket depth scale indicia represents the distance between the first indicia and the first tube first end minus a loop size indicated by the second loop size indicia plus the predetermined flip length. Multiple loop size indicia and associated socket depth indicia can be provided to provide socket depth readings for different loop sizes with a single instrument.

Preferably, the second tube has a graft implantation depth indicia thereon and wherein the measuring block has an associated second indicator associated therewith to provide a reading of a depth of implantation of a graft into the bone tunnel. In such case the reading on the implantation depth scale indicia preferably represents the distance between first indicia and the first tube first end minus the loop size indicated by the loop size indicia.

A method according to the present invention provides for measuring a depth of a socket portion of a bone tunnel in an ACL reconstruction. The method comprises the steps of: creating a pilot hole through a femur so that the pilot hole has a first end at a condylar notch surface of the femur and a second end at a superior portion of the femur, the pilot hole being oriented along a path desired for a replacement ligament in the femur; positioning a measuring pin so that a first indicia on the measuring pin is located at the pilot hole first end and a second end of the measuring pin extends out of the pilot hole second end; placing a first tube over the measuring pin such that a portion of the measuring pin is coaxially received therein and a first end of the first tube abuts the femur at the pilot hole second end; abutting the second end of the measuring pin against an abutment on a measuring block having a distance scale indicia thereon, the measuring block having a lateral dimension larger than a largest lateral dimension of the measuring pin; and reading a desired depth for the socket portion of the bone tunnel from the distance scale indicia, the socket portion extending from the pilot hole first end along the path defined by the pilot hole.

Preferably, the pilot hole is created with the measuring pin. Also preferably, an indicator is associated with the first tube, and the indicator provides the reading on the distance scale.

Preferably, the desired depth read on the distance scale correlates to a distance separating the first tube first end and the first indicia on the measuring pin, more specifically the desired depth represents the distance separating the first tube first end and the first indicia on the measuring pin minus a predetermined loop size plus a predetermined flip length. Preferably, the predetermined loop size is indicated adjacent the distance scale.

The method preferably further comprises the step of drilling the socket portion into the femur to the indicated depth from the condylar notch along the path. The method preferably further comprises the steps of: suspending the graft over a loop of the predetermined loop size, the loop being connected to an elongated bar; passing the elongated bar lengthwise through the bone tunnel and positioning the bar against the superior portion of the femur in a sideways orientation to prevent its passage back into the bone tunnel leaving the loop depending down into the socket portion and the graft suspended at least partially in the socket portion from the loop. The predetermined flip length is a distance beyond the femur sufficient to manipulate the bar from its lengthwise orientation into its sideways orientation after is has been passed through the tunnel and with the loop depending back into the tunnel.

Preferably, a further reading is made of an implantation depth length of the implant in the socket portion from a socket depth indicia associated with the first tube, the implantation depth representing the distance separating the first tube first end and the first indicia on the measuring pin minus the predetermined loop size.

BRIEF DESCRIPTION OF THE DRAWINGS

In what follows, preferred embodiments of the invention are explained in more detail with reference to the drawings, in which.

DETAILED DESCRIPTION

Figure 1:
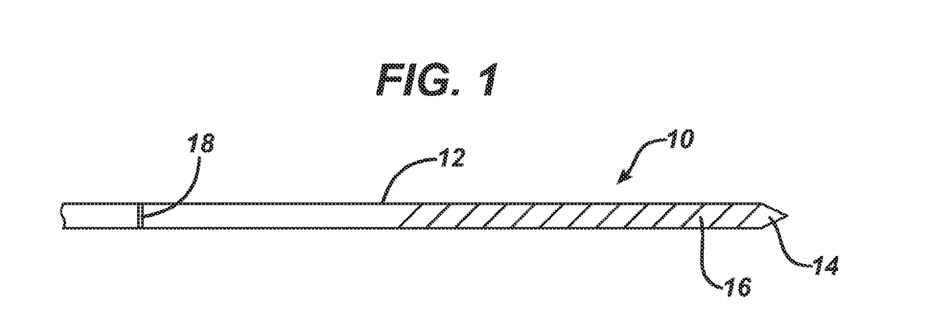
FIG. 1 is a side elevation view of a first embodiment of a beath pin according to the present invention.
Figure 1A:
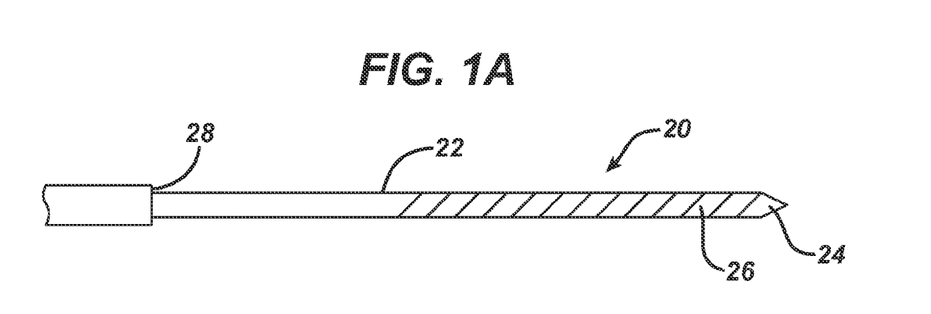
FIG. 1A is a side elevation view of a second embodiment of a beath pin according to the present invention.
Figure 1B:
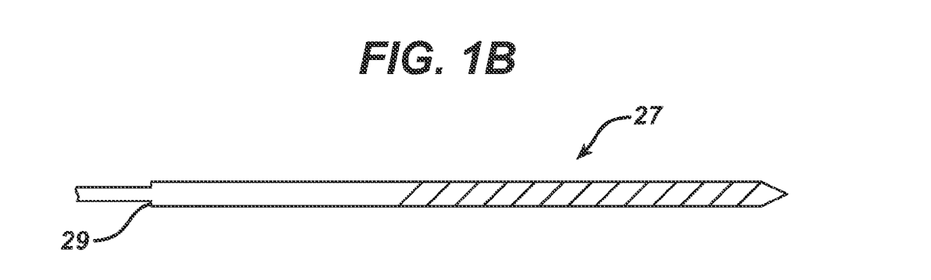
FIG. 1B is a side elevation view of a further embodiment of a beath pin according to the present invention.
Figure 2:
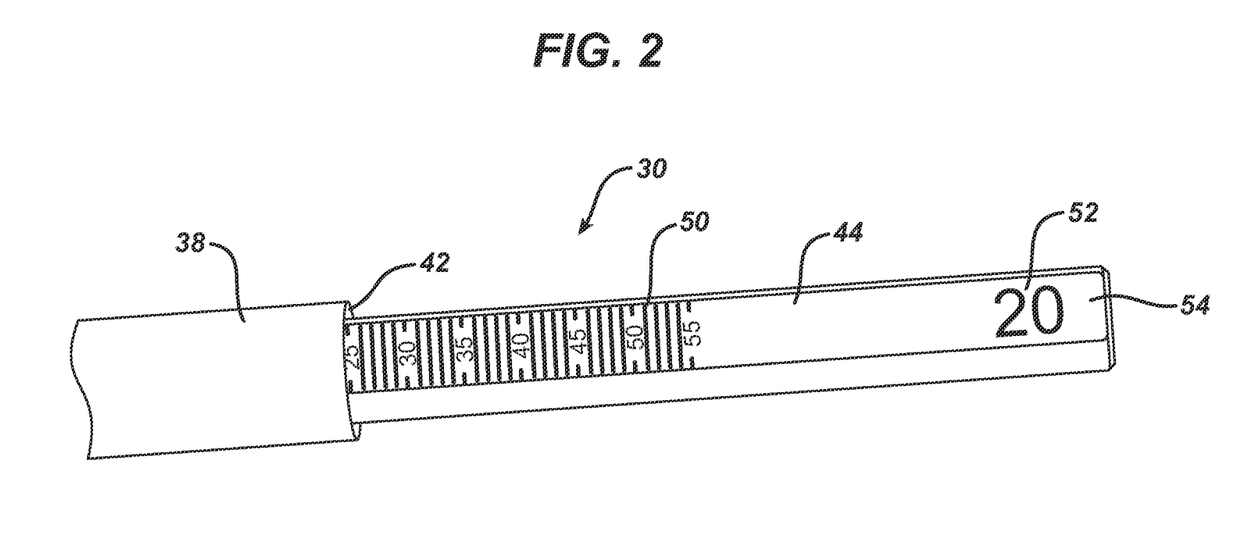
FIG. 2 is a side elevation view of a portion of a depth gauge according to the present invention.
Figure 3:
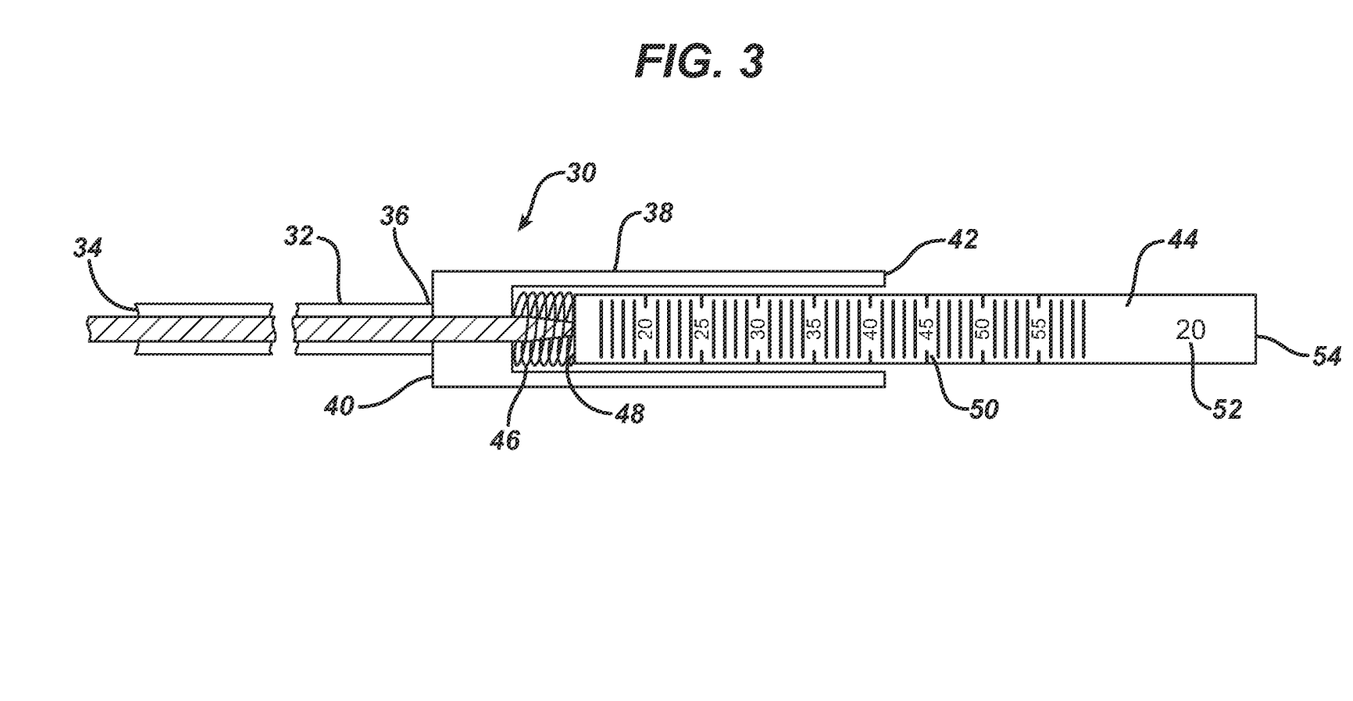
FIG. 3 is a side elevation view in cut-away of the depth gauge of FIG. 2.

FIGS. 1 to 3 illustrate primary components of the present invention. FIG. 1 depicts a beath pin 10 having an elongated body 12, sharp distal tip 14, optional drill flutes 16 adjacent the distal tip 14 and a laser etched depth indicia 18 located about 15 cm from the distal tip 14. FIG. 1A depicts an alternative beath pin 20 having an elongated body 22, sharp distal tip 24, drill flutes 26 adjacent the distal tip 24 and an annular flange 28 in place of the laser etched depth indicia 18 of the beath pin 10. The pins 10 or 20 will be passed into a femur (not shown in FIGS. 1 to 3, to either the indicia 18 or the flange 28 and the flange provides a tactile feedback to a surgeon that the correct depth of passage into the femur has occurred. FIG. 1B depicts an alternative beath pin 27 having a reverse annular flange 29 that provides a visual feedback that the correct depth of passage into the femur has occurred. The reverse flange 29 also allows the beath pin 27 to be removed by pulling it through the passage forwardly and out of the femur.

FIGS. 2 and 3 illustrate a depth gauge 30 for measuring and sizing the tunnel in the femur. The gauge comprises an elongated cylindrical first tube 32 sized to accommodate the beath pin 10, the first tube 32 has a first end 34 and a second end 36 attached to a larger second tube 38. The second tube 38 has a first end 40 attached to the first tube 32, a free second end 42. The second end 36 may be releasably attached via threads, snaps, bayonet fittings, or other means to the second tube 38 to allow the tube 32 to be disposable. A measuring block 44 travels within the second tube 38 and is preferably biased toward the first end 40 by a tension spring 46. A first end 48 of the measuring block 44 acts as an abutment against the tip 14 of the beath pin 10. It can be slightly countersunk for more positive engagement. A depth indicia scale 50 is provided on the measuring block and a loop size indicia 52 is provided toward a second end 54 of the measuring block 44.

The beath pins 10, 20 and 27 are preferably of small diameter, such as 2.4 mm. Markings thereon would be quite difficult to see due to its small size and could become obscured by body tissue. The measuring block 44 has an increased size making reading the indicia scale 50 easy. Preferably, the measuring block 44 has a width of at least 8 mm. The present arrangement also covers the sharp distal tip 14 of the beath pin 10 to enhance safety.

Figure 3A:
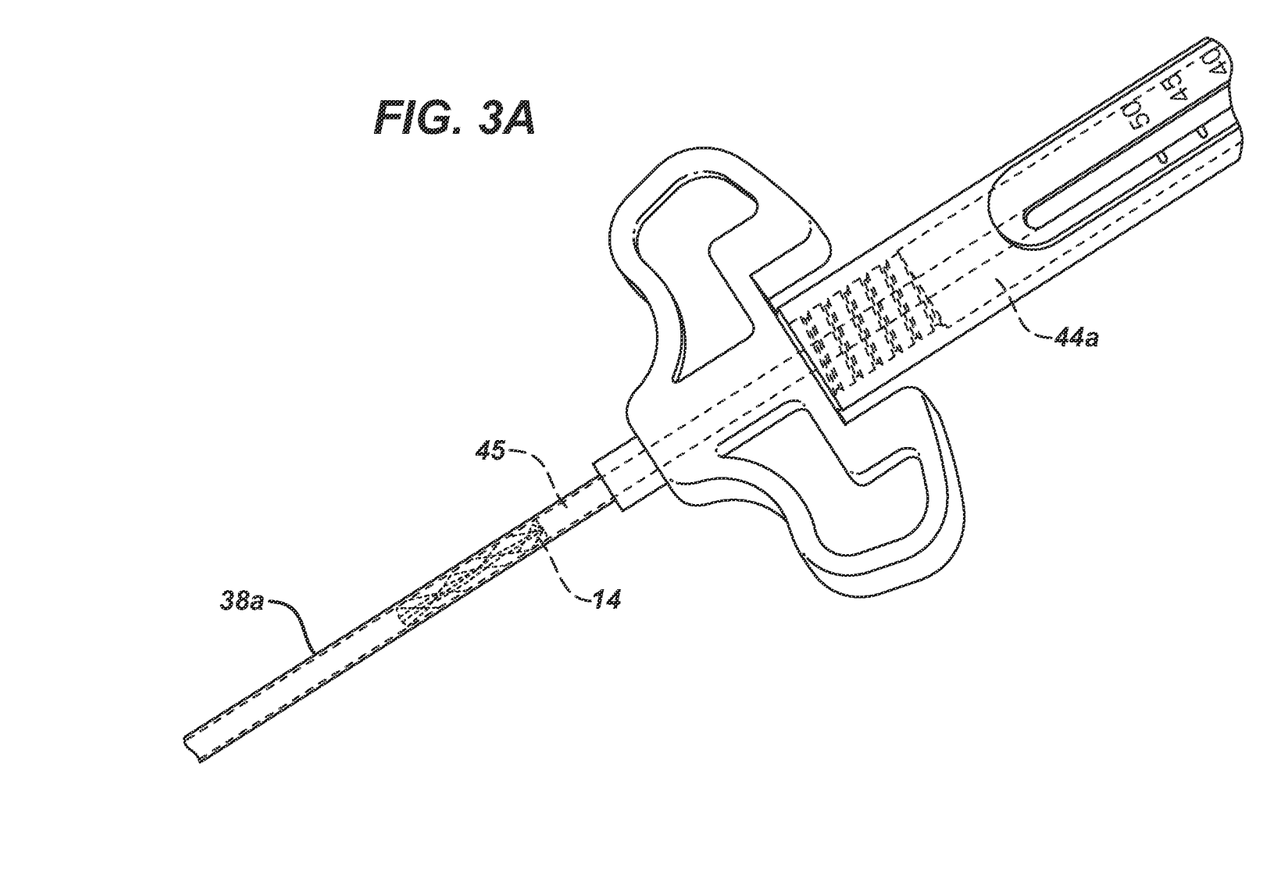
FIG. 3A is a perspective view in partial phantom of a second embodiment of a depth gauge according to the present invention.
Figure 3B:
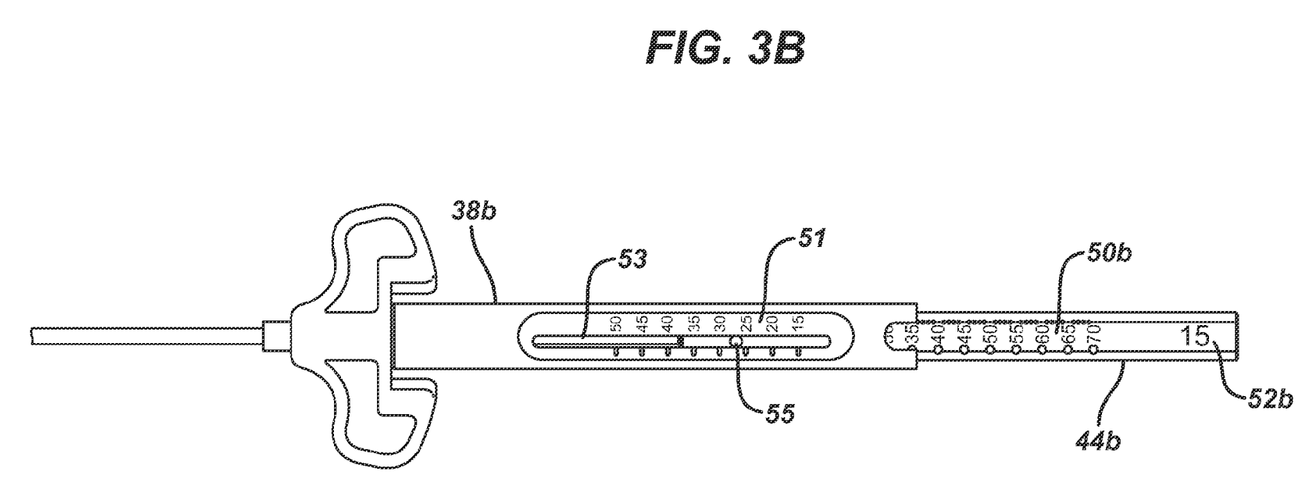
FIG. 3B is a side elevation view of a further embodiment of a depth gauge according to the present invention.

FIGS. 3A and B depict an alternative embodiments in which similar parts are identified with similar numerals with the subscripts "a" and "b" respectively. In FIG. 3A, a measuring block 44a has a projection 45 extending into the second tube 38a and it is against this projection 45 which the beath pin tip 14 abuts. This provides for a shorter and thus safer beath pin. In FIG. 3B a second tube 38b is provided with an additional marking scale 51 on a window 53 through which can be seen an indicator 55 on a measuring block 44b. The marking scale 51 indicates the length of the graft disposed within the femur as will be discussed ahead. Additionally, the measuring block 44b and second tube 38b can be provided with multiple faces disposed circumferentially thereabout, each with its own corresponding indicia scale 50b, additional marking scale 51 and loop size indicia 52b. For instance, one face could be arranged to work with a 20 mm loop size, a second face with a 25 mm loop size etc. with the loop size indicia 52b, indicia scale 50b and additional scale 51 arranged accordingly.

Figure 4:
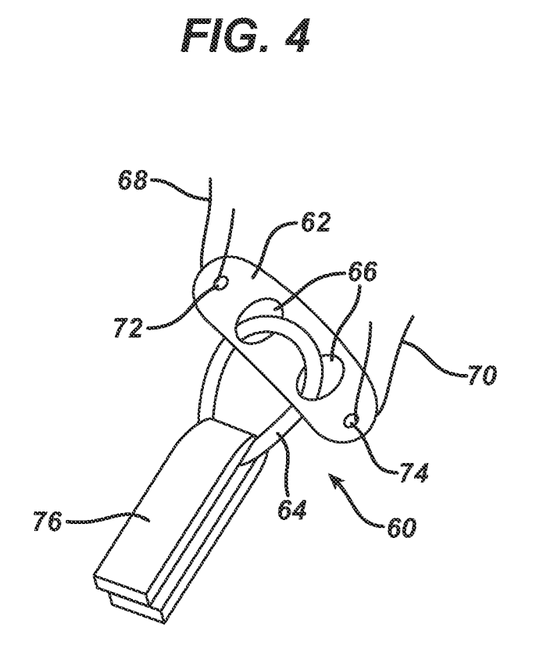
FIG. 4 is a perspective view of a graft construct for use in the procedure according to the present invention.
Figure 5:
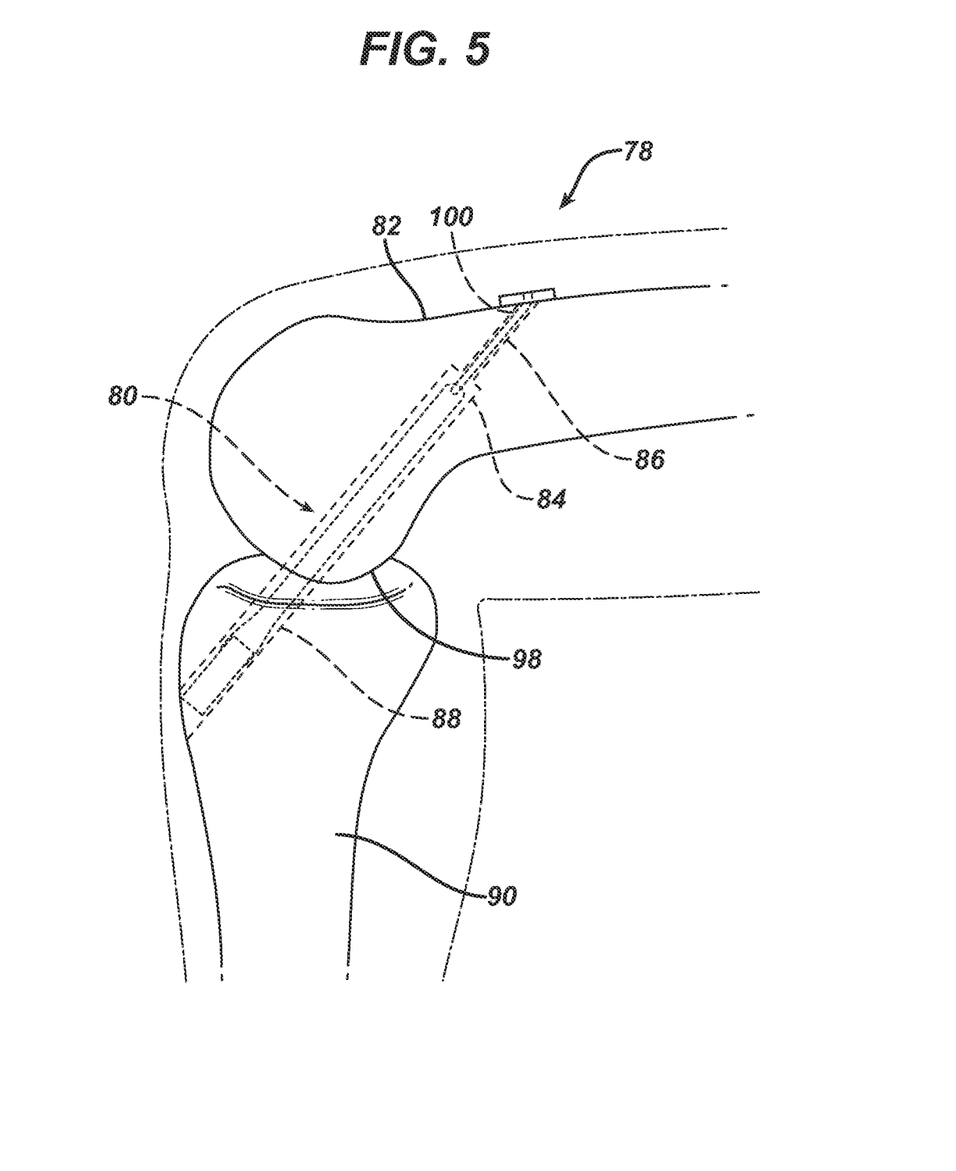
FIG. 5 is a side elevation view in cut-away of a knee having an ACL reconstruction according to the present invention.
Figure 6:
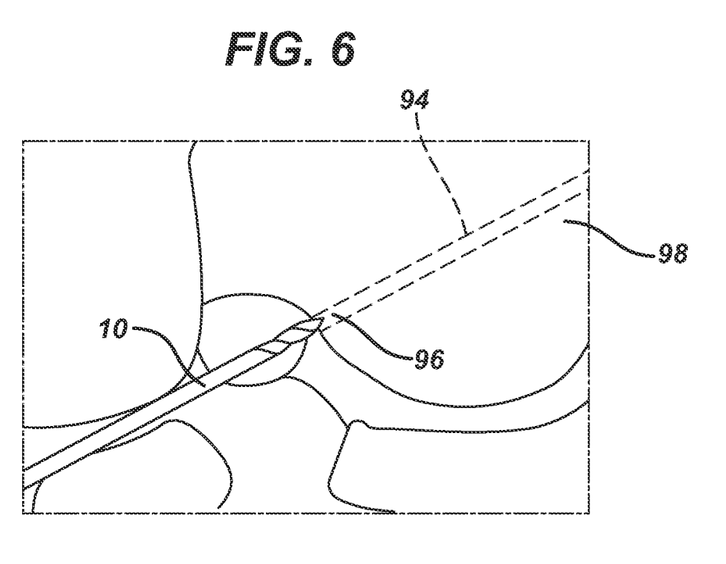
FIG. 6 is a front elevation view of a femur of the knee of FIG. 5 showing the creation of a pilot hole using the beath pin of FIG. 1.
Figure 7:
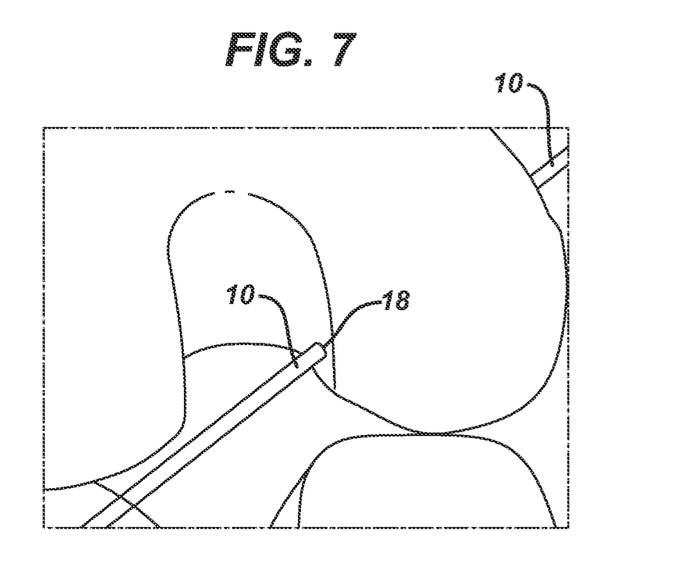
FIG. 7 is a front elevation view of a femur of the knee of FIG. 5 showing the beath pin of FIG. 1 inserted to a predetermined depth.
Figure 8:
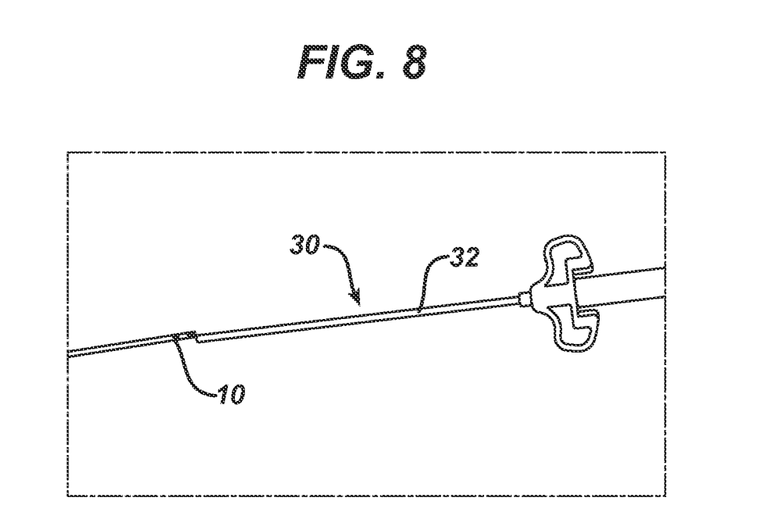
FIG. 8 is a perspective view of the depth gauge of FIGS. 2 and 3 being placed onto the beath pin.
Figure 9:
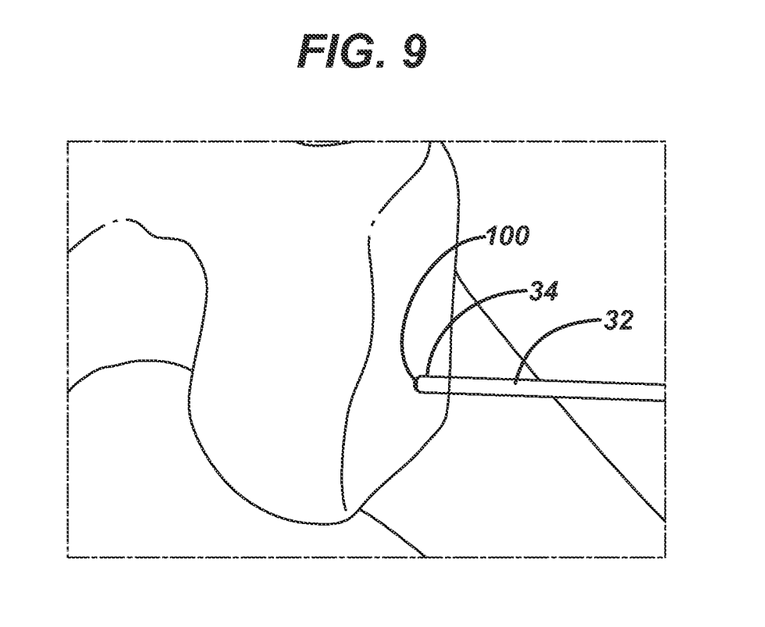
FIG. 9 is a perspective view of the depth gauge and beath pin of FIG. 8 with an end of the depth gauge engaging a surface of the femur.

FIG. 4 illustrates a graft construct 60 comprising an elongated bar 62 having a thick suture loop 64 through a pair of central openings 66 along with first and second guiding sutures 68 and 70 through first and second outside holes 72 and 74 respectively. A replacement graft 76 is looped over the loop 64. FIG. 5 illustrates the graft construct 60 in place in a patient's leg 78. A tunnel 80 in the leg's femur 82 comprises a larger diameter inferior portion or socket 84 sized to accommodate the graft 76 and a smaller diameter superior portion or passing channel 86 sized to accept the bar 62 in a lengthwise orientation. The bar 62 sits against the femur 82 in a sideways orientation with the loop 64 depending down through the passing channel 86 and into the socket in which is placed the graft 76. An opposite end of the graft 76 is placed into a tibial tunnel 88 in the leg's tibia 90 and held in place with an anchor 92 such as the INTRAFIX® anchor available from DePuy Mitek Inc. of Raynham, Mass.

FIGS. 6 to 13 illustrate measurement and creation of the tunnel 80. First a beath pin 10 is drilled in the desired orientation through the femur 82 creating a pilot hole 94 therethrough. The pin 10 is then advanced until the laser mark 18 is flush with the surface femur 82 (See FIGS. 6 and 7). An appropriate sized gauge 30 is selected based upon the length of the loop 64, with that size being printed 52 on the gauge 30. Alternatively, if the gauge 30 has multiple faces with indicias 50 etc. as heretofore described the appropriate loop size face is oriented toward the surgeon. The first tube 32 of the gauge 30 is passed over the beath pin 10 and advanced until its first end 34 abuts the femur (See FIGS. 8 and 9). The puts the beath pin through the femur 82 along the path (the pilot hole 94) which the soon to be drilled tunnel 80 will follow with the laser mark 18 at an inferior end 96 of the pilot hole 94 at a condylar notch surface 98 of the femur 82 and with the gauge first tube first end 34 at an opposite superior end 100 of the pilot hole 94.

Figure 10:
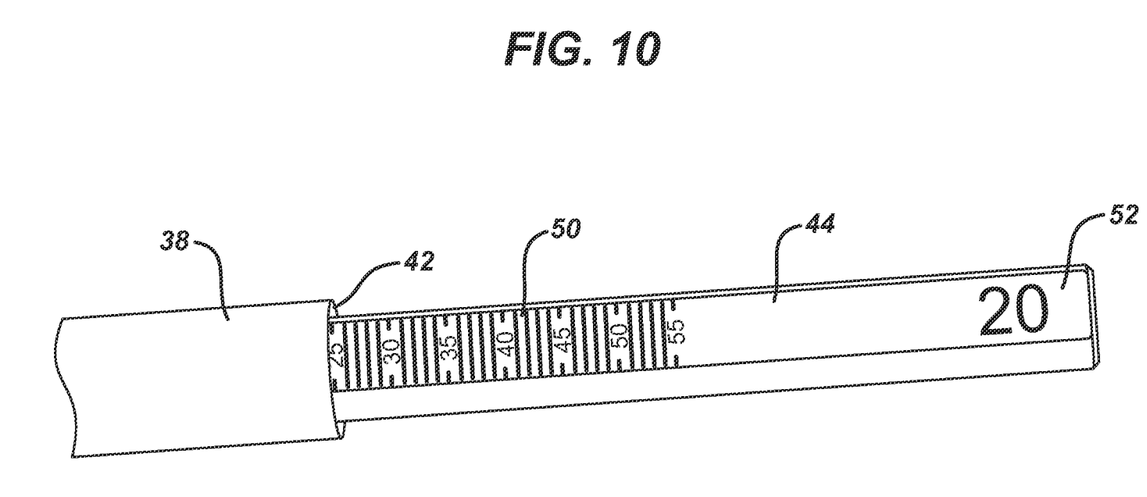
FIG. 10 is a side elevation view of the depth gauge of FIG. 8 showing the indicated reading for socket depth.
Figure 11:
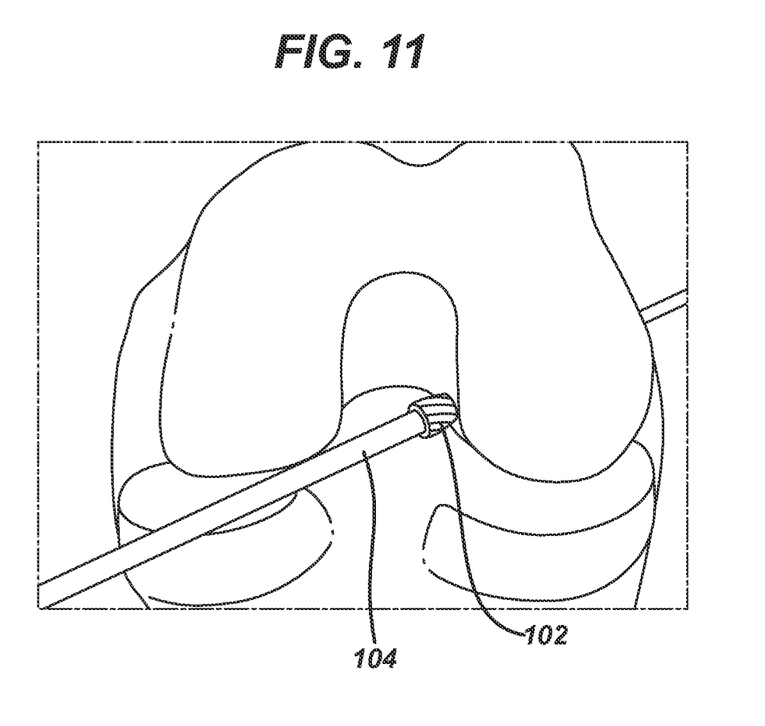
FIG. 11 is a front elevation view of the femur of the knee of FIG. 5 showing the socket being drilled.
Figure 12:
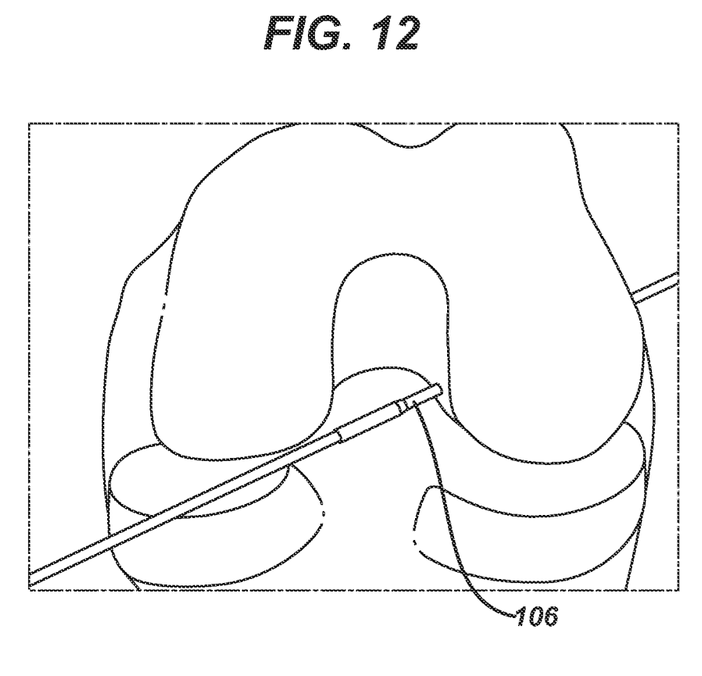
FIG. 12 is a front elevation view of the femur of the knee of FIG. 5 showing the passing channel being drilled.
Figure 13:
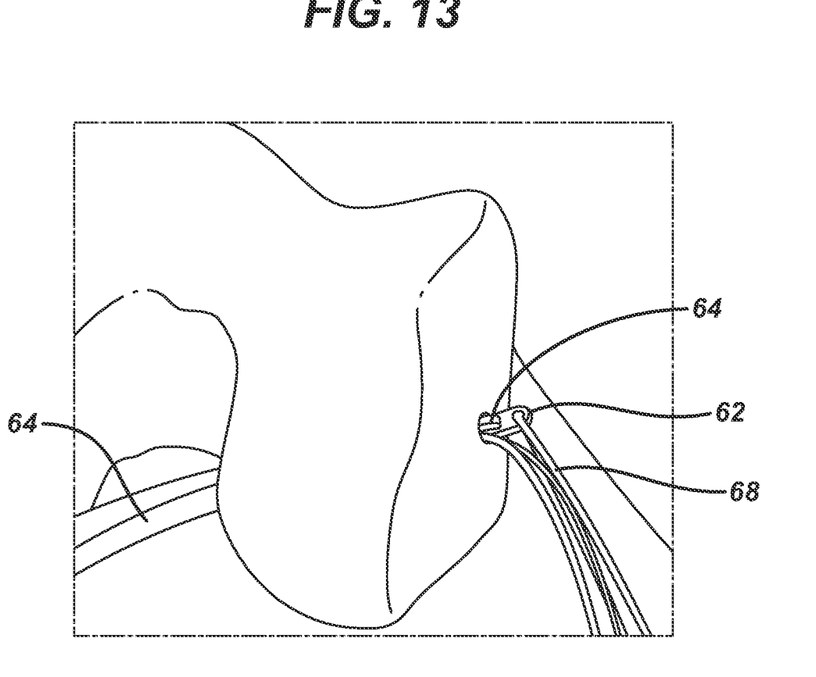
FIG. 13 is a front elevation view of the femur of the knee of FIG. 5 showing the graft construct being passed.

The distal tip 14 of the pin 10 abuts the measuring block first end 48 and pushes the measuring block 44 out of the second tube 38 against the resistance of the spring 46 and the indicia scale 50 can be read at the second tube second end 42 (see FIGS. 3 and 10). It returns the desired depth of the socket 84 from the condylar notch surface. A cannulated drill 102 of appropriate diameter for the socket 84 and having drilling depth indicia 104 thereon is passed over the beath pin 10 and the socket is drilled to the appropriate depth as indicated by the indicia scale 50 (see FIG. 11). Then a separate, smaller cannulated drill 106 is passed over the pin 10 and the passing channel 86 is drilled through the femur 82 (see FIG. 12). The graft construct 60 is then pulled up through the tunnel 80 with the bar 62 in a lengthwise orientation via the first suture 68 and then the bar 62 is manipulated into a sideways orientation via the second suture 70 and placed into abutment against the femur 82.

The depth gauge 30 provides the surgeon with the necessary information to drill the socket 84 for a given loop size. The length of the tunnel 80 is determined by the anatomy of the femur 82 and the path of the tunnel 80 therethrough. The gauge 30 measures this length by the spacing of the laser mark 18 and the gauge first tube first end 34. This spacing is then translated into an appropriate socket 84 depth by the size and orientation of parts of the gauge 30. The gauge 30 determines this depth by subtracting the loop length from the total length and then adding a length sufficient to allow the bar 62 to be pulled free of the femur and flip its orientation, about 8 to 10 mm. The graft length in the socket 84 shown by the scale 51 represents the socket 84 depth minus the flipping length. Rather than the surgeon having to perform calculations the gauge scales are oriented to read out the proper socket depth and graft length in the tunnel for a given loop size.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An instrument for determining a depth of a bone tunnel in an ACL reconstruction, the instrument comprising:
    a measuring pin having an elongated body having a first end and a first indicia spaced apart from the first end;
    a first tube which co-axially receives the first end of the measuring pin body, the first tube having in internal diameter sized to accommodate the measuring pin body first end, an open first end and a second end;
    a second tube at the first tube second end; the second tube having an internal diameter larger than the first tube internal diameter and an first end connected to the first tube second end;
    a measuring block disposed at least partially within the second tube, the measuring block having an abutment and a socket depth scale indicia thereon;
    a first indicator on the second tube; the first indicator and the socket depth scale indicia being oriented such that when the measuring pin body first end abuts the measuring block abutment the alignment of the indicator and the socket depth scale indicia provides a reading indicative of a desirable depth of the bone tunnel,
    a loop size indicia, wherein the reading on the socket depth scale indicia represents the distance between the first indicia and the first tube first end minus a loop size indicated by the loop size indicia plus a predetermined flip length.

2. An instrument according to claim 1 wherein the measuring block is biased toward the first tube.

3. An instrument according to claim 1 wherein the first indicator is the second tube second end.

4. An instrument according to claim 1 and further comprising a second loop size indicia indicating a different value than the loop size indicia and a second socket depth indicia associated therewith.

5. An instrument according to claim 4 wherein the reading on the socket depth scale indicia represents the distance between the first indicia and the first tube first end minus a loop size indicated by the loop size indicia plus a predetermined flip length and the reading on the second socket depth scale indicia represents the distance between the first indicia and the first tube first end minus a loop size indicated by the second loop size indicia plus the predetermined flip length.

6. An instrument according to claim 1 wherein the second tube has a graft implantation depth indicia thereon and wherein the measuring block has an associated second indicator associated therewith to provide a reading of a depth of implantation of a graft into the bone tunnel.

7. An instrument according to claim 4 wherein the reading on the implantation depth scale indicia represents the distance between first indicia and the first tube first end minus the loop size indicia.

* * * * *